US010624558B2

United States Patent
Ceccaldi et al.

(10) Patent No.: US 10,624,558 B2
(45) Date of Patent: Apr. 21, 2020

(54) PROTOCOL INDEPENDENT IMAGE PROCESSING WITH ADVERSARIAL NETWORKS

(71) Applicant: Siemens Healthcare GmbH, Erlangen (DE)

(72) Inventors: Pascal Ceccaldi, Princeton, NJ (US); Benjamin L. Odry, West New York, NJ (US); Boris Mailhe, Plainsboro, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 50 days.

(21) Appl. No.: 16/055,546

(22) Filed: Aug. 6, 2018

(65) Prior Publication Data

US 2019/0046068 A1 Feb. 14, 2019

Related U.S. Application Data

(60) Provisional application No. 62/543,600, filed on Aug. 10, 2017.

(51) Int. Cl.
*A61B 5/055* (2006.01)
*G06N 3/08* (2006.01)
(Continued)

(52) U.S. Cl.
CPC .......... *A61B 5/055* (2013.01); *G06K 9/4628* (2013.01); *G06K 9/6268* (2013.01); *G06K 9/6271* (2013.01); *G06N 3/0454* (2013.01); *G06N 3/084* (2013.01); *G06T 7/10* (2017.01); *G06T 7/11* (2017.01); *G06T 9/002* (2013.01); *G06T 11/003* (2013.01); *G06K 2209/05* (2013.01); *G06T 2207/10088* (2013.01); *G06T 2207/20081* (2013.01); *G06T 2207/20084* (2013.01); *G06T 2207/30016* (2013.01)

(58) Field of Classification Search
CPC ........ A61B 5/055; G06T 7/207; G06N 3/084; G06N 7/02
See application file for complete search history.

(56) References Cited

U.S. PATENT DOCUMENTS

2017/0147944 A1* 5/2017 Csurka ................. G06N 3/0454
2018/0024968 A1* 1/2018 Clinchant ............ G06N 3/0454
                                                                706/12
(Continued)

OTHER PUBLICATIONS

Arjovsky, Martin, Soumith Chintala, and Léon Bottou. "Wasserstein gan." arXiv preprint arXiv:1701.07875, pp. 1-32, (2017).
(Continued)

*Primary Examiner* — Diane D Mizrahi

(57) ABSTRACT

Systems and methods are provided for generating a protocol independent image. A deep learning generative framework learns to recognize the boundaries and classification of tissues in an MRI image. The deep learning generative framework includes an encoder, a decoder, and a discriminator network. The encoder is trained using the discriminator network to generate a latent space that is invariant to protocol and the decoder is trained to generate the best output possible for brain and/or tissue extraction.

7 Claims, 8 Drawing Sheets

(51) Int. Cl.
*G06T 7/10* (2017.01)
*G06T 9/00* (2006.01)
*G06T 11/00* (2006.01)
*G06N 3/04* (2006.01)
*G06K 9/62* (2006.01)
*G06T 7/11* (2017.01)
*G06K 9/46* (2006.01)

(56) References Cited

U.S. PATENT DOCUMENTS

2019/0049540 A1* 2/2019 Odry .................... G06N 3/0454
2019/0325621 A1* 10/2019 Wang .................... A61B 6/032

OTHER PUBLICATIONS

Arora, Sanjeev, et al. "Generalization and equilibrium in generative adversarial nets (gans)." arXiv preprint arXiv:1703.00573, pp. 1-27, (2017).

Eskildsen, Simon F., et al. "BEaST: brain extraction based on nonlocal segmentation technique." NeuroImage 59.3 (2012): 2362-2373.

Gulrajani, Ishaan, et al. "Improved training of wasserstein gans." Advances in Neural Information Processing Systems, pp. 1-11, 2017.

Iglesias, Juan Eugenio, et al. "Robust brain extraction across datasets and comparison with publicly available methods." IEEE transactions on medical imaging 30.9 (2011): 1617-1634.

Isola, Phillip, et al. "Image-to-image translation with conditional adversarial networks." arXiv preprint, pp. 1-10, (2017).

Leung, Kelvin K., et al. "Brain MAPS: an automated, accurate and robust brain extraction technique using a template library." Neuroimage 55.3 (2011): 1091-1108.

Radford, Alec, Luke Metz, and Soumith Chintala. "Unsupervised representation learning with deep convolutional generative adversarial networks." arXiv preprint arXiv:1511.06434, pp. 1-16, (2015).

Sadananthan, Suresh A., et al. "Skull stripping using graph cuts." NeuroImage 49.1 (2010): 225-239.

Smith, Stephen M. "Fast robust automated brain extraction." Human brain mapping 17.3 (2002): 143-155.

Ségonne, Florent, et al. "A hybrid approach to the skull stripping problem in MRI" Neuroimage 22.3 (2004): 1060-1075.

* cited by examiner

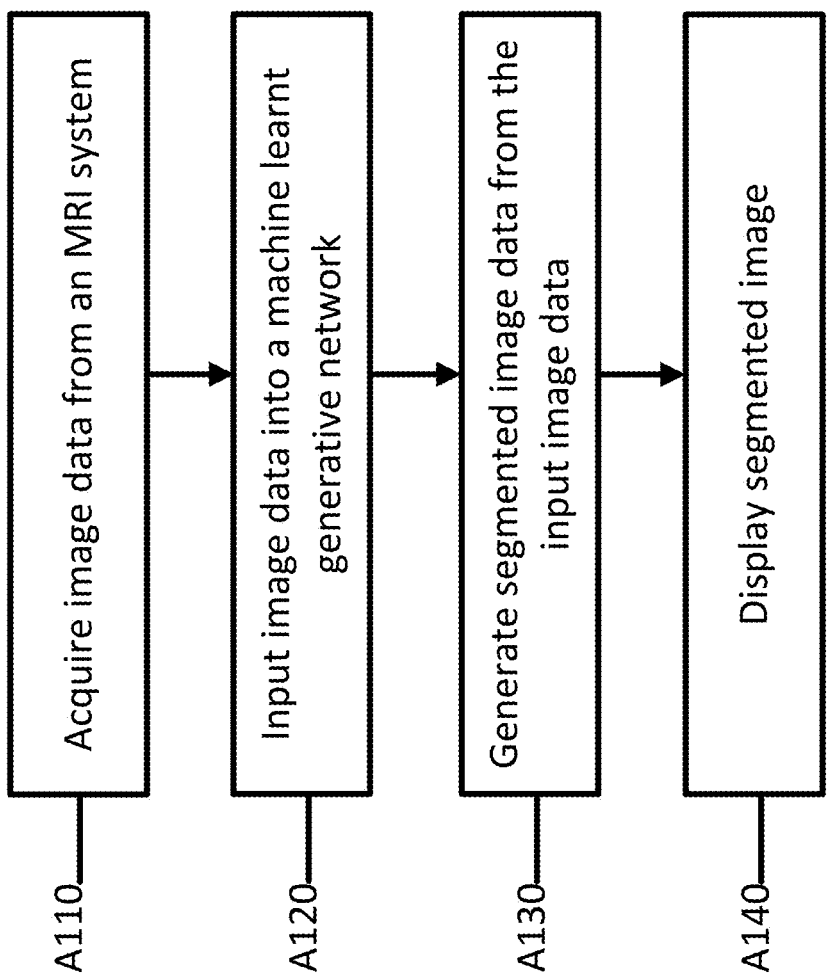

PROTOCOL INDEPENDENT IMAGE PROCESSING WITH ADVERSARIAL NETWORKS

CROSS REFERENCE TO RELATED APPLICATIONS

This application claims the benefit of U.S. Provisional Application No. 62/543,600, filed Aug. 10, 2017, which is hereby incorporated by reference in its entirety.

FIELD

The present embodiments relate to medical image processing.

BACKGROUND

Variations in MRI acquisition protocols and machinery result in different appearances of tissue in acquired image data. Image intensities in MRI do not have a fixed meaning, even within the same protocol for the same body region obtained on the same scanner for the same patient. The variations between scans, scanner, protocols, etc. present issues in image display, segmentation, and quantification.

For example, for an MRI scan of the brain, preprocessing enables extraction of the brain and its main tissues. Several approaches address extraction of the brain and brain tissues. Methods such as boundary region based, atlas based, and machine learning based segmentation approaches have been used. However, the results are often unequal due to the variations in acquired data, for example, a level of brightness or color depending on the sequence and the protocol the input data was acquired in. In an example, the results of segmentation by two physicians may differ because of the differences in the physician's training in MRI data acquisition. Different machines, different sequences, or different settings may provide different intensities. Different environmental conditions may lead to different results even from the same machine or patient from scan to scan.

SUMMARY

By way of introduction, the preferred embodiments described below include methods and systems for generating a protocol independent image. A deep learning generative framework is provided that learns to recognize the boundaries of the brain in the head as well as its main tissues. The deep learning generative framework includes an encoder, a decoder, and a discriminator network. The encoder is trained to generate a latent space that is invariant to protocol and the decoder is trained to generate the best output possible for brain and/or tissue extraction.

In a first aspect, a method is provided for generating domain independent magnetic resonance images in a magnetic resonance imaging system. A patient is scanned by the magnetic resonance imaging system to acquire magnetic resonance data. The magnetic resonance data is input to a machine learnt generator network trained to extract features from input magnetic resonance data and reconstruct domain independent images using the extracted features. The machine learnt generator network generates a domain independent segmented magnetic resonance image from the input magnetic resonance data. The domain independent magnetic resonance image is displayed.

In a second aspect, a method is provided for training a generator neural network to output segmented MR images. First data acquired from an MRI system is input into an encoder network of the generator neural network. The encoder network is configured to generate a latent space that represents a compact version of the first data. The latent space is input into a decoder network of the generator neural network. The decoder network is configured to generate a first segmented image. A first value is calculated by the decoder network based on a comparison of the segmented image and a ground truth segmented image. The latent space is input into a discriminator network. The discriminator network is configured to classify the latent space as acquired from a first domain or second domain. The discriminator network calculates a second value based on a second loss function for the classification. The encoder network is adjusted as a function of the first value and second value. Inputting, inputting, calculating, inputting, calculating, and adjusting are repeated until a training loss converges.

In a third aspect, a system is provided for generating domain independent magnetic resonance images. The system includes a magnetic resonance system, a generator network, a memory, and a display. The magnetic resonance system is configured to acquire magnetic resonance data for a patient. The generator network is configured with a discriminator network and a critic function to generate domain independent magnetic resonance image data. The memory is configured to store the generator network as trained. The display is configured to display the domain independent magnetic resonance image data from the generator network.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 3 a method for providing protocol independent image processing for a magnetic resonance imaging system according to an embodiment.

DETAILED DESCRIPTION

A machine learnt network is used to provide protocol and domain independent processing of MRI data. The machine learnt network is trained using ground truth data from multiple domains to identify invariant features. The machine network learns to integrate the differences between protocols and domains and retain features that are specific to the task of segmentation and independent from the protocols and domains.

Figure 1:
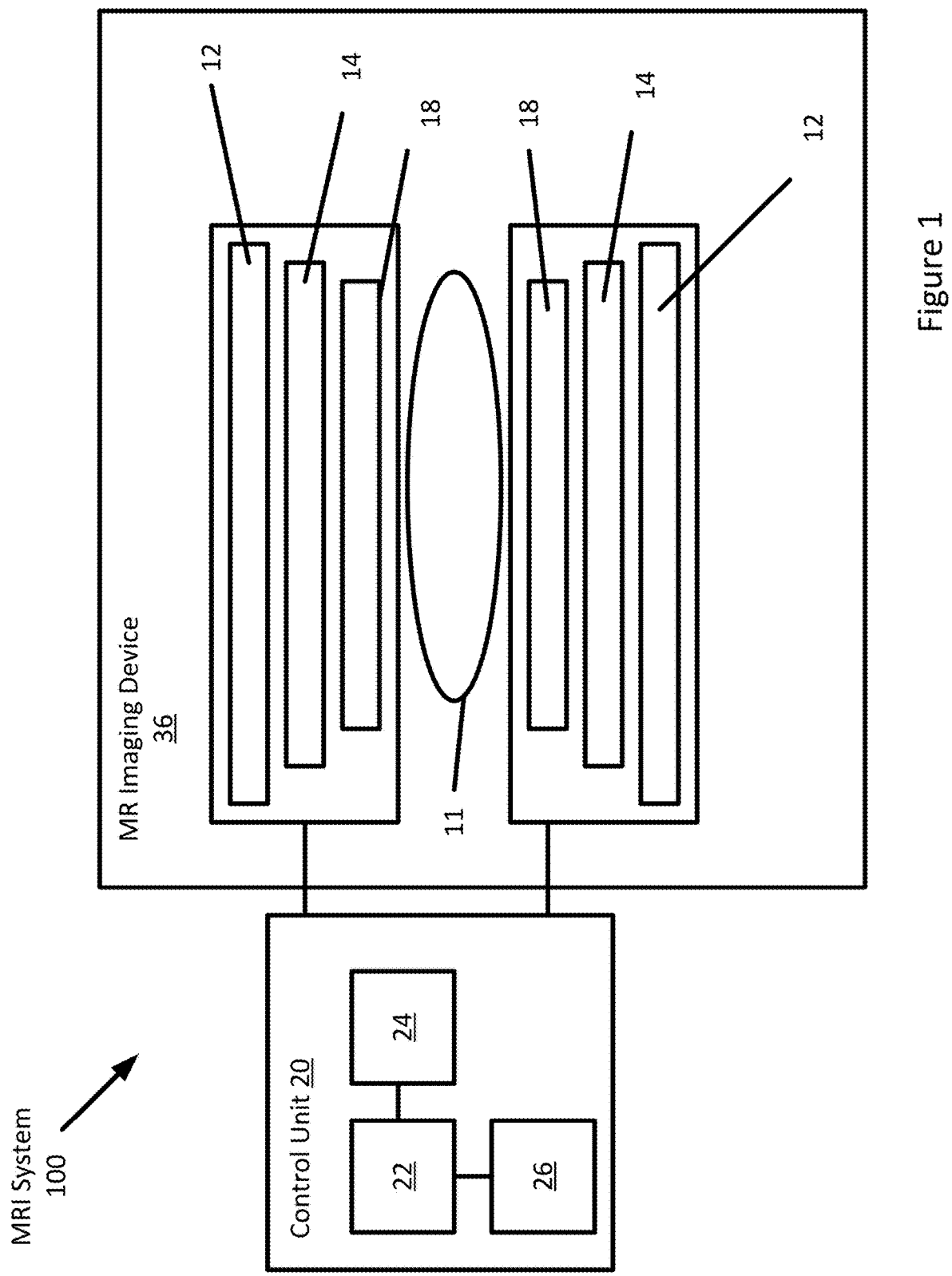
FIG. 1 depicts an example MRI system.

FIG. 1 depicts an MRI system 100 for acquisition of frequency domain components representing Magnetic Resonance (MR) image data for storage in a storage array. The MRI system 100 includes a control unit 20 that is configured to process the MR signals and generate images of the body for display to an operator. The control unit 20 may store the MR signals and images for later processing or viewing in a memory 24. The control unit 20 may include a display 26 for presentation of images to an operator. The MR scanning system 100 is only exemplary, and a variety of MR scanning systems may be used to collect the MR data.

In the MRI system 100, magnetic coils 12 create a static base or main magnetic field in the body of patient 11 or an object positioned on a table and imaged. Within the magnet system are gradient coils 14 for producing position dependent magnetic field gradients superimposed on the static magnetic field. Gradient coils 14, in response to gradient signals supplied thereto by a gradient and control unit 20, produce position dependent and shimmed magnetic field gradients in three orthogonal directions and generate magnetic field pulse sequences. The shimmed gradients compensate for inhomogeneity and variability in an MR imaging device magnetic field resulting from patient anatomical variation and other sources.

The control unit 20 may include a RF (radio frequency) module that provides RF pulse signals to RF coil 18, which produces magnetic field pulses that rotate the spins of the protons in the imaged body of the patient 11 by ninety degrees or by one hundred and eighty degrees for so-called "spin echo" imaging, or by angles less than or equal to 90 degrees for "gradient echo" imaging. Gradient and shim coil control modules in conjunction with RF module, as directed by control unit 20, control slice-selection, phase-encoding, readout gradient magnetic fields, radio frequency transmission, and magnetic resonance signal detection, to acquire magnetic resonance signals representing planar slices of the patient 11.

In response to applied RF pulse signals, the RF coil 18 receives MR signals, e.g. signals from the excited protons within the body as the protons return to an equilibrium position established by the static and gradient magnetic fields. The MR signals are detected and processed by a detector within RF module and the control unit 20 to provide an MR dataset to an image data processor 22 for processing into an image. In some embodiments, the image data processor 22 is located in the control unit 20, in other embodiments, the image data processor 22 is located remotely. A two or three-dimensional k-space storage array of individual data elements in a memory 24 of the control unit 20 stores corresponding individual frequency components including an MR dataset. The k-space array of individual data elements includes a designated center, and individual data elements individually include a radius to the designated center.

A magnetic field generator (including coils 12, 14 and 18) generates a magnetic field for use in acquiring multiple individual frequency components corresponding to individual data elements in the storage array. The individual frequency components are successively acquired using a Cartesian acquisition strategy as the multiple individual frequency components are sequentially acquired during acquisition of an MR dataset. A storage processor in the control unit 20 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized.

Imaging data for MR may be defined by two different relaxation times—T1 and T2. T1 (longitudinal relaxation time) is the time constant that determines the rate at which excited protons return to equilibrium (e.g. a measure of the time taken for spinning protons to realign with the external magnetic field). T2 (transverse relaxation time) is the time constant that determines the rate at which excited protons reach equilibrium or go out of phase with each other. T2 is a measure of the time taken for spinning protons to lose phase coherence among the nuclei spinning perpendicular to the main field.

Three common MRI sequences used are T1-weighted, T2-weighted, and FLAIR (Fluid Attenuated Inversion Recovery). T1-weighted images are produced by using short TE and TR times. The contrast and brightness of the image are predominately determined by T1 properties of tissue. Conversely, T2-weighted images are produced by using longer TE and TR times. In the images, the contrast and brightness are predominately determined by the T2 properties of tissue. The Flair sequence is similar to a T2-weighted image except that the TE and TR times are very long. By doing so, abnormalities remain bright but normal CSF fluid is attenuated and made dark.

Each different sequence provides different image results. For example, the brightness of tissues is different for each sequence. In addition to different MRI sequences, differences between different systems may also generate different image data. An MRI system from a first manufacturer may provide slightly different results than an MRI system from a second manufacturer. Even among similar machines, results may vary due to degradation over time, technician preferences, and environmental conditions among other factors.

For automatic segmentation, extraction, classification, or diagnosis, the differences in brightness, shade, or color output of pixels may lead to errors when analyzing the data. The output data from an MRI system may be processed to for analysis or diagnosis. Processing may include, for example, segmentation and classification. The goal of segmentation is to divide an image into a set of semantically meaningful, homogeneous, and nonoverlapping regions of similar attributes such as intensity, depth, color, or texture. The segmentation result is either an image of labels identifying each homogeneous region or a set of contours which describe the region boundaries. For brain MRI analysis, image segmentation is used for measuring and visualizing the brain's anatomical structures, for analyzing brain changes, for delineating pathological regions, and for surgical planning and image-guided interventions. Classification involves assigning elements (e.g. pixels or voxels) in the image a tissue class. The problems of segmentation and classification are interlinked because segmentation implies a classification, while a classifier implicitly segments an image. In the case of brain MRI, image elements are typically classified into three main tissue types: white matter (WM), gray matter (GM), and cerebrospinal fluid (CSF). The segmentation results are further used in different applications such as for analyzing anatomical structures, for studying pathological regions, for surgical planning, and for visualization among other uses.

Due to the differences in different domains with different sequences, settings, environments, technicians, and other factors, different outcomes may be generated by different MRI domains. The differences in output images may lead to poor diagnostics. Different outcomes from different domains may prohibit accurate image processing.

Figure 2C:
FIGS. 2A, 2B, and 2C depict example images of MR data acquired using different sequences.
Figure 2B:
Figure 2A:
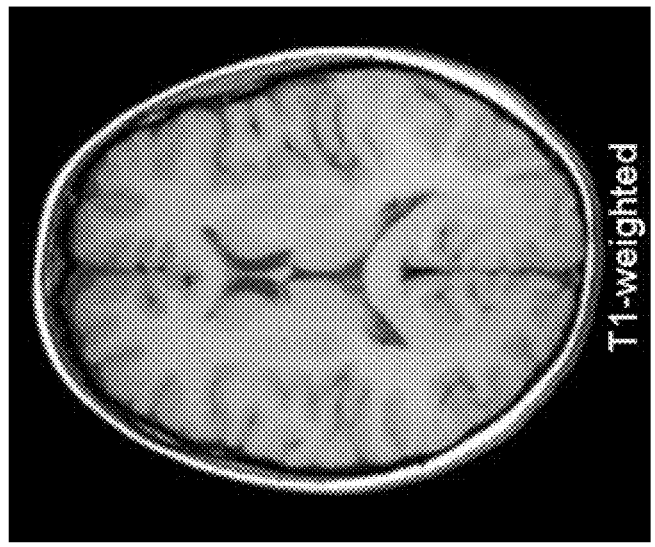

FIGS. 2A, 2B, and 2C depict an example of three results from MRI systems. FIG. 2A depicts a T1-weighted image. FIG. 2B depicts a T2-weighted image. FIG. 3C depicts a Flair image. The images may be acquired from the same patient at or around the same time using similar equipment. However, due to the sequences, the output images include different levels of brightness. The differences in the data may prohibit accurate or efficient processing of the image data.

Embodiments provide a semi-supervised deep learning approach that provides a machine learnt network to identify the differences between protocols and therefore retain features that are specific to the task and independent from the protocols. The disclosed machine learnt networks may be implemented to computationally facilitate processing of medical imaging data and consequently improving and optimizing medical diagnostics.

FIG. 3 depicts an example method for providing protocol independent image processing for a magnetic resonance imaging system. The acts are performed by the system of FIG. 1, FIG. 5, FIG. 8, other systems, a workstation, a computer, and/or a server. Additional, different, or fewer acts may be provided. For example, for segmentation, an initialization act may be performed prior to inputting the MR data. A smoothing act may be performed after the segmented data 439 is output. The machine learnt networks may be trained, e.g. configured, prior to the method of FIG. 3. The acts are performed in the order shown (e.g., top to bottom) or other orders.

At act A110, an object is scanned by the magnetic resonance imaging system to acquire MR data. As depicted and described in FIG. 1 above, the MR data may be acquired using MR scanners. For example, gradient coils, a whole-body coil, and/or local coils generate a pulse or scan sequence in a magnetic field created by a main magnet or coil. The whole-body coil or local coils receive signals responsive to the re-orientation of molecules shifted due to the scan sequence. In an embodiment and used as an example below, the MR data may represent image data for a brain of a patient. Different objects, organs, or regions of a patient may also be scanned.

The MR data is k-space data or image data. Image data is MR data after Fourier transform into object space. The image data may be at any point after transform, so may be scalar values or may be formatted as RGB values for a display screen. The MR data may be scan data to be used to generate an image on a display. The acquired MR data may be data being processed to generate an image, data formatted for display, or data that has been used to display. The MR data may be data with no or some image processing.

The MR data may represent volumes. Three-dimensional datasets are obtained. As k-space data, information content may be provided that is responsive to a three-dimensional distribution of locations, but the data itself does not directly represent the locations prior to transform. In alternative embodiments, two-dimensional datasets representing or responsive to tissue in planes are obtained. In other embodiments, sequences of MR data responsive to the same tissue over time are acquired for training.

Alternative methods may be used to acquire the MR data. The MR data may be acquired remotely from the server or workstation or may be acquired at a different time, for example, hours or days prior to the processing provided below in Acts A120-A140. The MR data may be stored locally onsite or offsite, for example in the cloud.

In an embodiment, the MR data may be input into an initialization stage prior to being input into the machine learnt generator network. The initialization stage may include different architecture and may vary between being a single layer in the machine learnt generator network defining a number of feature maps to start with from the input MR data directly, or the initialization state may be a full generative network that is trained with the machine learnt generator, for example, serving as a normalization stage.

At act A120, the MR data is input to a machine learnt generator network trained to generate a protocol independent extraction and segmentation of MR data. The machine learnt generator may be configured to perform either extraction, segmentation, or both. In an embodiment, the machine learnt generator network is a fully convolutional dense network. In an embodiment, the generator extracts features from the MR data and reconstructs, in an example of MR data for a head region of a patient, a segmentation of the brain and its tissue. The generator includes an encoder that generates a latent space, e.g. a compact representation of the input MR data. The latent space includes values that describe distilled features of the input MR data. The generator also includes a decoder that uses the latent space generated by the encoder to reconstruct the object and masks, for example brain and tissue masks. In an embodiment, the encoder and decoder are symmetrical, using the same number of pooling (downsampling/upsampling) layers. The symmetrical structures provide for connections between encoding and decoding stages referred to as skip connections. The skip connections help against vanishing gradients and help maintain the high frequency components of the images. Between each pooling step, blocks are defined as succession of layers that also use skip connections. The number of layers in each block may be defined and a growth rate set to increase the number of feature maps for each consecutive layer in a block.

Figure 4:
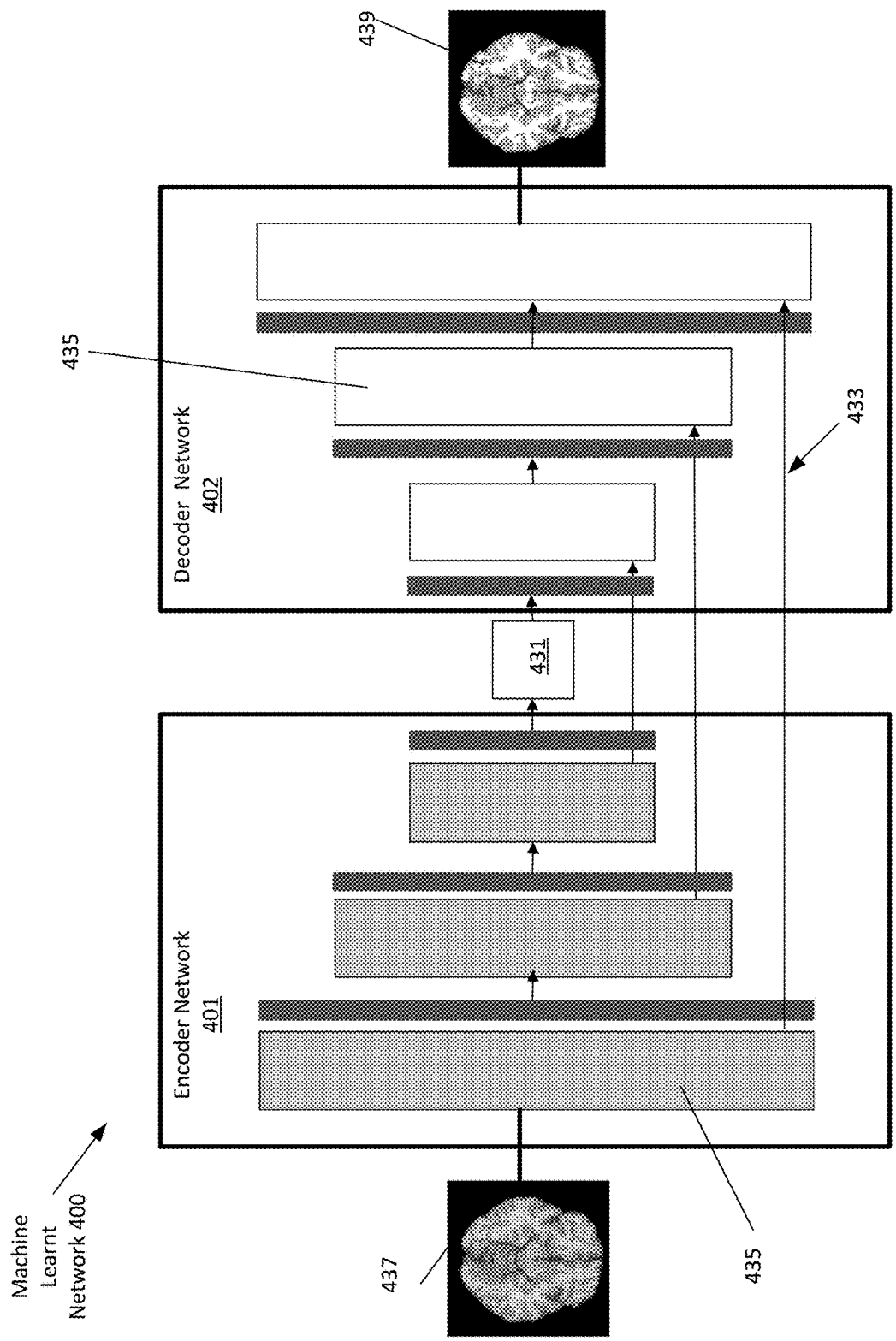
FIG. 4 depicts a machine learnt generator network according to an embodiment.

FIG. 4 depicts an example machine learnt network 400. The machine learnt network 400 is defined as a plurality of sequential feature units or layers 435. The machine network inputs MR data 437 (here depicted as an image) and outputs segmented data 439. The machine learnt network 400 includes an encoder 401 and a decoder 402. The encoder 401 and decoder each include layers 435 that encode or decode respectfully. Sequential is used to indicate the general flow of output feature values from one layer 435 to input to a next layer 435. The information from the next layer 435 is fed to a next layer 435, and so on until the final output. The layers may only feed forward or may be bi-directional, including some feedback to a previous layer 435. The nodes of each layer 435 or unit may connect with all or only a sub-set of nodes of a previous and/or subsequent layer 435 or unit. Skip connections 433 may be used, such as a layer 435 outputting to the sequentially next layer 435 as well as other layers.

Various units or layers may be used, such as convolutional, pooling (e.g., max pooling), deconvolutional, fully connected, or other types of layers. Within a unit or layer 435, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed-convolution to reconstruct, the level of abstraction reverses. Each unit or layer 435 in the encoder 401 reduces the level of abstraction or compression while each unit or layer 435 in the decoder increases the level of abstraction.

The generator network may further be configured as a SegNet including an encoder network and a corresponding decoder network. Each encoder layer 435 has a corresponding decoder layer 435. The final decoder output is fed to a classifier to produce class probabilities for each pixel independently. Each encoder in the encoder network performs convolution with a filter bank to produce a set of feature maps. The decoder network up samples input feature maps using the memorized max-pooling indices from the corresponding encoder feature maps producing sparse feature maps. The sparse feature maps are then convolved with a decoder to produce dense feature maps. A batch normalization step is then applied to each of the maps. The high dimensional feature representation at the output of the final decoder is input to a classifier which classifies each pixel independently. The output of the classifier is a X channel image of probabilities where X is the number of classes. The predicted segmentation corresponds to the class with maximum probability at each pixel.

The network may be a DenseNet. The DenseNet connects each layer to every other layer 435 in a feed-forward fashion. For each layer 435 in the DenseNet, the feature-maps of all preceding layers are used as inputs, and the output feature-map of that layer 435 is used as input into all subsequent layers. In the DenseNet, for each layer 435, the feature maps of all preceding layers are used as inputs, and its own feature maps are used as inputs into all subsequent layers. To reduce the size of the network, the DenseNet may include transition layers. The layers include convolution followed by average pooling. The transition layers reduce height and width dimensions but leave the feature dimension the same. The machine learnt generator network may further be configured as a U-net. The U-Net is an auto-encoder in which the outputs from the encoder-half of the network are concatenated with the mirrored counterparts in the decoder-half of the network. The skip connections 433 prevent the middle of the network from becoming a bottleneck.

Other network arrangements may be used, such as a support vector machine. Deep architectures include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (e.g., including different weights for all regions of an image). The training of CNN is entirely discriminative through back-propagation. DBN, on the other hand, employs the layer-wise unsupervised training (e.g., pre-training) followed by the discriminative refinement with back-propagation if necessary. In an embodiment, the arrangement of the machine learnt network is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

Rather than pre-programming the features and trying to relate the features to attributes, the deep architecture of the machine network is defined to learn the features at different levels of abstraction based on an input image data with or without preprocessing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

The training of the machine learnt network 400 includes teaching the network to both output segmented data 439 that is similar to ground truth segmented data and also to output protocol independent data. In an embodiment, the training is performed by adjusting weights in the machine network as a function of a loss function from both the decoder network (e.g. the difference between the segmented data 439 and ground truth data) and a loss function from an adversarial network that is trained to discriminate between domain specific features of the encoder network 401. The updated loss using the Domain Adaptation becomes:

$$L_{tot} = L_{seg}(\theta_{enc} + \theta_{dec}) - \alpha L_{disc}(\theta_{enc} + \theta_{disc})$$

where $\alpha$ is a weight to balance the effect of the domain adaptation.

Figure 5:
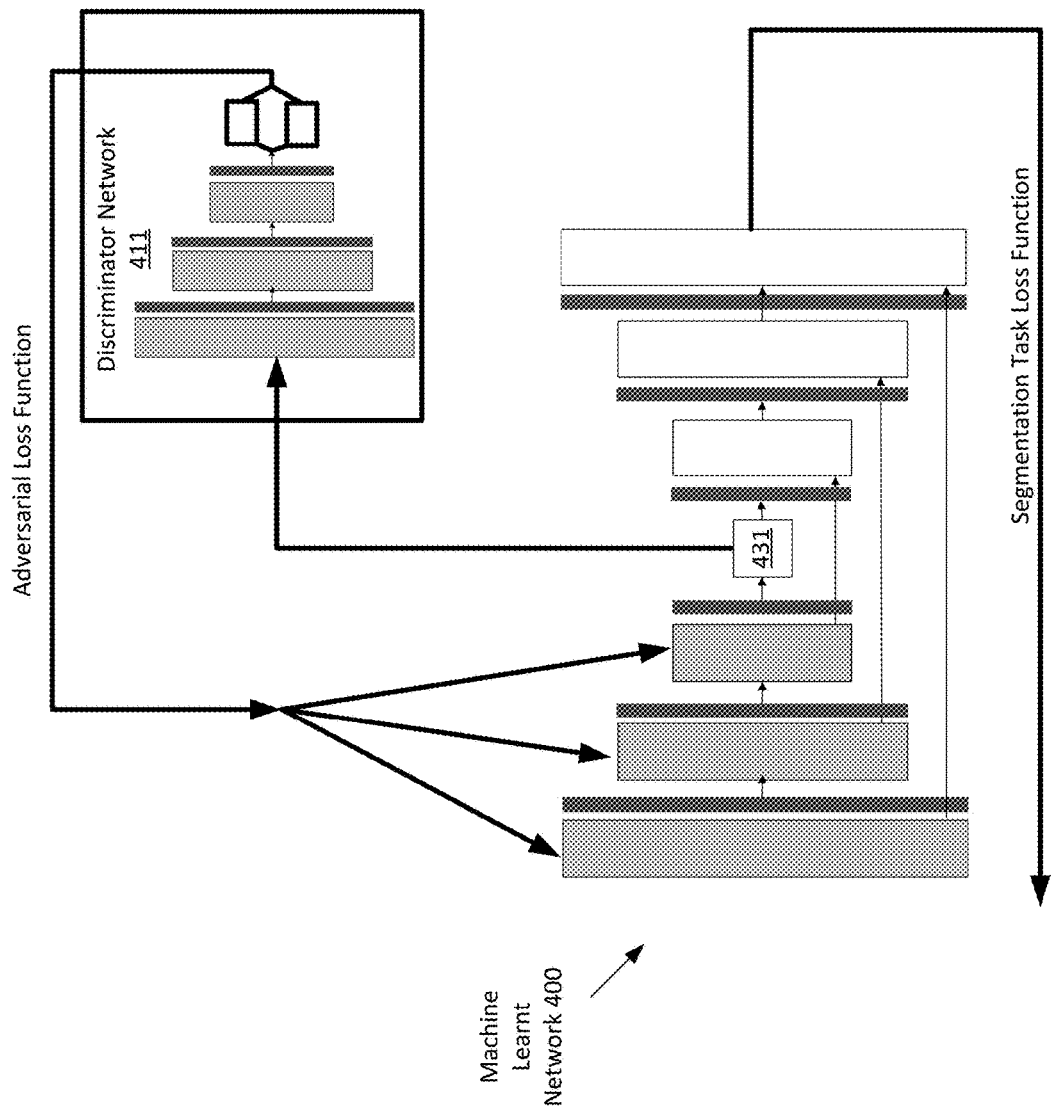
FIG. 5 depicts a diagram for training a machine learnt network according to an embodiment.

FIG. 5 depicts an example diagram for training the machine learnt network 400 400. The machine learnt network 400 is trained to both learn the invariant features using the adversarial network for domain classification and also the segmentation task. The adversarial network is used to make the encoder-generated features invariant to the protocol differences. Using the latent space features, a discriminator network 411 is used to find out whether the features comes from one domain (one protocol) or another. The optimization drives the discriminator to maximize its loss, and such that it becomes unable to recognize which protocol or domain the data comes from. Training may be done sequentially, with one batch of data with segmentation ground truth with data from original domain and the other one with domain ground truth. In an embodiment, the initial domain is the one that has data with most details, as the initial domain may be easier to adapt to less detailed acquisition.

In one method of training the segmentation task, weights of the encoder and decoder are initialized using one or more known techniques. Stochastic gradient descent (SGD) with a fixed learning rate and momentum is used for the learning sequence (e.g. the training loss). The training loss is calculated as a difference between a ground truth image and the output segmented image. Ground truth images may be acquired using MRI procedures and subsequently manually segmented (or automatically segmented using other methods). The network is trained until the training loss converges. Other methods and loss functions may be used to train the segmentation task.

Figure 6:
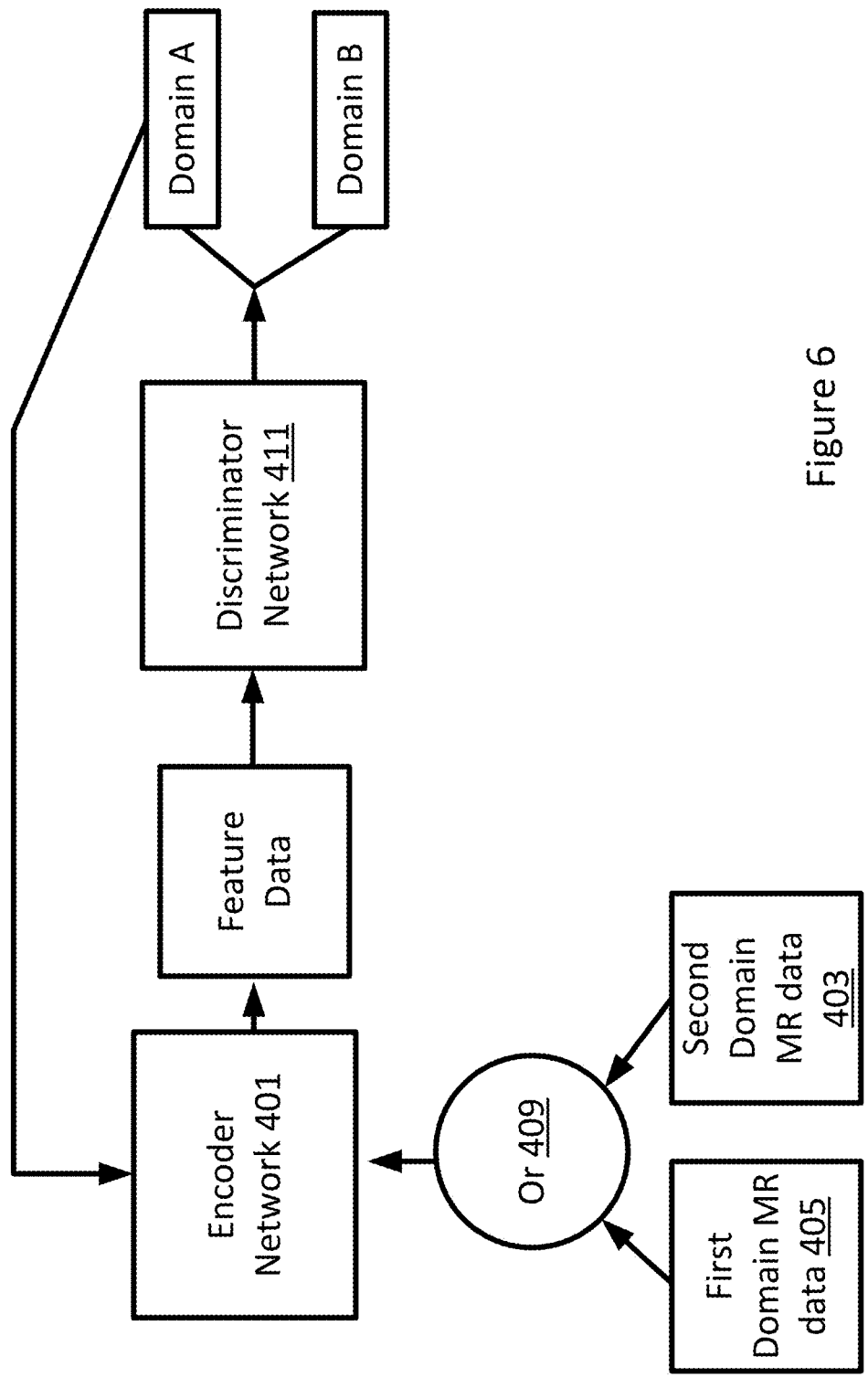
FIG. 6 depicts an example adversarial process for training a machine learnt network.

The discriminator network 411 may be trained using an adversarial process. FIG. 6 depicts an example adversarial process. FIG. 6 depicts the encoder network 401 and a discriminator network 411. The inputs, e.g. training data, for the adversarial network are the MR data from two different domains, e.g. a first and second domain. The two domains may be different machines, different settings, different sequences, different technicians, etc. The Encoder network 401 inputs the MR data and generates a feature map as described above. The encoder network 401 may generate features maps at each level including the output latent space 431. The features data (e.g. maps, latent space 431) is input into the discriminator network 411 which attempts to discern from which domain the features maps were generated from. The discriminator network 411 classifies feature data as either from one domain or another and then provides feedback for the encoder network 401. In the adversarial process, the encoder network 401 may be trained to minimize the sum of two losses: a supervised L1 distance of the encoder prediction $E\{x,y\}$ $\|y-G(x)\|L1$, and an unsupervised adversarial term $E\{x\}$ $D(G(x))$. The adversarial term is provided by the discriminator network 411. While the encoder network 401 is being trained, the discriminator network 411 is also adjusted to provide better feedback to the encoder network 401.

As depicted in FIG. 6, the adversarial process uses the training process as a contest between the two separate networks: the encoder network 401 that generates feature data 407 and the discriminator network 411 that attempts to classify the input data as either from Domain A or Domain B. During training, the OR function 409 randomly feeds the encoder network 401 first domain MR data or second domain MR data. The first domain MR data may be considered ground truth data for which the discriminator network 411 attempts to distinguish the data from the second domain. The discriminator network 411 detects a difference and provides feedback to the encoder network 401. Based on the feedback, the encoder network 401 adjusts one or more weights. The information from the discriminator network 411 is backpropagated to the encoder network 401, so the encoder network 401 identifies whether or how to adapt weights in order to generate feature data that may fool the discriminator network 411. At the end of training, the encoder network 401 is able to generate feature data for the second domain that is indistinguishable from feature data from the first domain. During training, the discriminator network 411 may be adjusted in order to get better at distinguishing the two domains.

The discriminator network 411 may use probability distributions or other methods to classify and distinguish between the two domains. The discriminator network 411 provides the information to the encoder network 401. The information provided by the discriminator network 411 may be in the form of a gradient that is calculated as a function of a comparison of the probability distributions of the feature data, e.g. comparing a first probability distribution of values for the first domain with the second domain. The gradient may include both a direction and a slope that steer updates for the generator network 401 in the right direction. After a number of iterations, the gradient directs the generator network 401 to a stable place where the generator network 401 is generating feature data that includes probability distributions that are similar between the two domains. The gradients provided by the discriminator network 411 change as the encoder network 401 generates and provides new feature data. Providing an informative and accurate gradient is key for the training process. If, for example, the discriminator network 411 is too good at distinguishing between the domains, the feedback may not be helpful to the encoder network 401. If the discriminator network 411 is provided with bad feature data or the encoder network 401 does not generate good feature data, the feedback may not be helpful.

During the training process, to avoid or limit one or more of the above referenced issues, the discriminator network 411 provides a gradient calculated using a Wasserstein distance. The Wasserstein distance is a measure of the differences between probability distributions. The Wasserstein value may also be referred to as the earth mover's distance. The two probability distributions may be interpreted as two different ways of piling up a certain amount of dirt over the region D. The earth mover's distance is the minimum cost of turning one pile into the other; where the cost is assumed to be amount of dirt moved times the distance by which it is moved. In another embodiment, the discriminator network provides a gradient calculated using a Cramer distance. Similar to the Wasserstein distance, the Cramer distance is a measure of the differences between probability distributions. The Cramer distance may be a measure of the energy required to transform one distribution into another.

The training may be repeated for multiple iterations until the networks reach a convergence or the encoder network 401 is able to generate feature data that is indistinguishable between domains. The training may be performed prior to the procedure of FIG. 3. At act A110, the encoder network 401 may already be fully trained to generate a segmented image. The machine learnt network 400 may be trained simultaneously to perform both the segmentation task and the domain adaptation. Alternatively, the machine network may be first trained on the domain adaptation and then the segmentation task or vice versa.

At act A130, the machine learnt network 400 generates segmented image data 439 from the input MR data 437. The segmented image data 439 may include boundaries for different types of tissues. For example, for segmented image data 439 for a brain, boundaries and classifications may be included for at least white matter, grey matter, and cerebrospinal fluid. Each pixel or voxel may be classified as a type of tissue. In the machine learnt network 400, for each encoder there may be a corresponding decoder network that up samples the feature map using memorized max-pooling indices. Sparse feature maps of higher resolutions are produced. The sparse maps are fed through a trained filter bank to produce dense feature maps. The last decoder layer is connected to a classifier that classifies each pixel. In an embodiment, a final smoothing step includes a layer with a kernel size of one that cleans up the images prior to output. The output image may identify the type of tissue depicted in the image. Different colors or shades of grey, for example, may be used to depict the segmented image. The output image may be annotated with additional information.

In an embodiment, a down sampled version of the input data can be used to first focus on the context (surrounding of the brain, general shape of the brain) for brain extraction. From this network output, a second network dealing with native or high resolution can be used to refine the segmentation. The network would be used only within the scope defined by the low resolution segmentation, within a band created around its boundaries (subtraction of dilated segmentation to eroded segmentation).

The encoder network 401 and decoder network may be periodically updated. For example, online or other updated learning is performed. As new samples are acquired, the learning may be repeated in total or to incorporate the further training data.

At act A140, an image of the segmented object is displayed to an operator. The output may be presented to an operator with labels or different colors representing different tissues or points of interest. The output may be two-dimensional or three-dimensional. The output may be color or black and white. The image data and the segmented image data 439 may be stored for later use.

In an embodiment, the method further includes a feature refinement step using adversarial training with a Wasserstein or Cramer distance on the decoder output. The adversarial training may be done end to end while the encoder is being trained or after the encoder is trained using the domain adaptation, thus focusing on refining the weights of the decoder. A conditional discriminator network may be used to refine the encoder/decoder. The conditional discriminator network identifies whether the segmentation that is presented as input is generated or ground truth. Ground truth data may be provided that is manually segmented (or automatically segmented and corrected).

The adversarial process uses the training process as a contest between the two separate networks: the machine network that generates segmented data 439 and the conditional discriminator network that attempts to classify the input data as either generated by the machine network or provided as ground truth (e.g. manually or alternatively segmented). An OR function randomly feeds the conditional discriminator network with either the segmented object or ground truth data. The conditional discriminator network detects a difference between the two sources and provides feedback to the machine network. Based on the feedback, the machine network adjusts one or more weights. The information from the conditional discriminator network is backpropagated to the machine network so that the machine network identifies whether or how to adapt weights in order to generate a segmented image that may fool the discriminator network. At the end of training, the machine learnt network 400 is able to generate a segmented object that is indistinguishable from ground truth segmented data. During training, the conditional discriminator network may be adjusted in order to get better at distinguishing the true images from generated images. In an embodiment, the conditional discriminator network may also use the raw MR data (e.g. input images) as input. The additional information from the input images may help the conditional discriminator determine if the input data is generated or ground truth.

In an embodiment, the conditional discriminator network may provide a gradient calculated using a Wasserstein distance. The Wasserstein distance is a measure of the differences between probability distributions. The Wasserstein value may also be referred to as the earth mover's distance. The two probability distributions may be interpreted as two different ways of piling up a certain amount of dirt over the region D. The earth mover's distance is the minimum cost of turning one pile into the other; where the cost is assumed to be amount of dirt moved times the distance by which it is moved. In another embodiment, the conditional discriminator network provides a gradient calculated using a Cramer distance.

Another approach is to synthesize the original image from the produced segmentation. An additional generative network is used to synthesize the original with a set of loss to minimize the errors between the original input and the synthesized input from generated segmentation.

Figure 7:
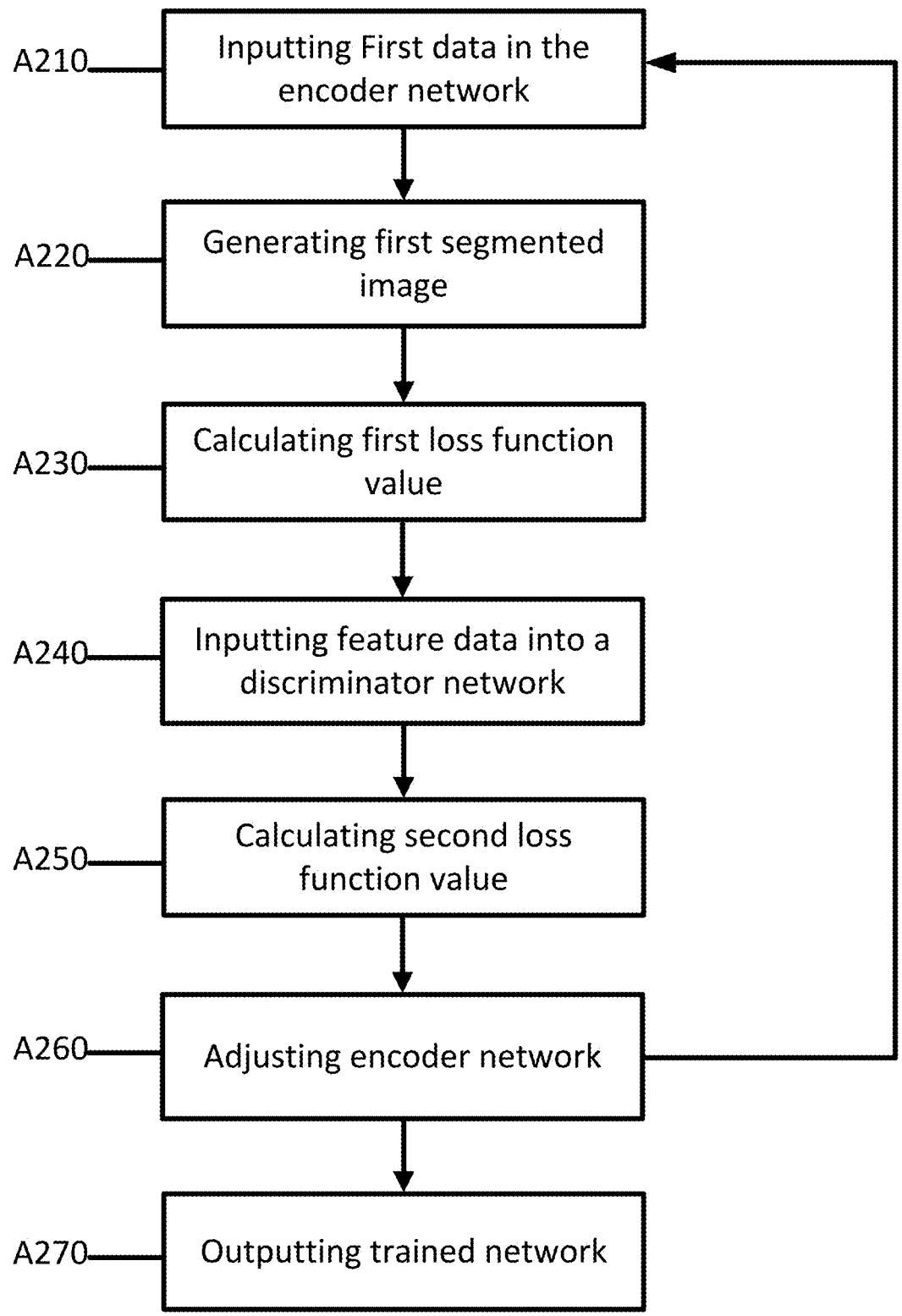
FIG. 7 depicts one embodiment of a method for training a machine network.

FIG. 7 depicts one embodiment of a method for training a machine learnt network 400 for generate a protocol independent feature extraction for MR data. The acts are performed by the system of FIG. 1, FIG. 5, FIG. 8, other systems, a workstation, a computer, and/or a server. The acts are performed in the order shown (e.g., top to bottom) or other orders.

The method of FIG. 7 trains an encoder network 401 to generate a feature map that is invariant to protocol and a decoder that is optimized to generate the best output possible for brain and/or tissue extraction. The training is to learn to output an image. The training may involve many iterations using a set of training data. The many samples in the training data are used to learn to output segmented image data 439 given input MR data. The output image is for spatially distributed locations, such as outputting scalar or display values for 2D or 3D locations. Once trained, the machine learnt network 400 (encoder/decoder) may be applied to generate a segmented image that is invariant to a protocol, sequence, or machine used to acquire the MR data. In other embodiments, the training continues. The machine network is periodically updated. For example, online or other updated learning is performed. As new samples are acquired, the learning is repeated in total or to incorporate the further training data.

At act A210, first data acquired from an MRI system is input into an encoder network 401 of a generator neural network 400. The encoder network 401 is configured to generate a latent space 431 that represents a compact version of the first data.

In an embodiment, a fully convolutional dense network is used for the generator neural network 400. The fully convolutional dense network includes an encoder and a decoder. The fully convolutional dense network first includes in an encoder that generates a latent space 431, or a compact representation of the input images. The encoder 401 is followed by a decoder 402 that uses the latent space 431 to get to the specific task of reconstructing the brain and tissue masks. The encoder 401 and decoder 402 are symmetrical, using the same number of pooling (downsampling/upsampling) steps and therefore allowing connections between encoding and decoding stages. Between each pooling step, blocks are defined as succession of layers which also use skip connections. The number of layers in each block can be defined and a growth rate is set to increase the number of feature maps for each consecutive layer 435 in a block.

In an embodiment, a convolutional-to-transposed-convolutional network is used. One segment (i.e., encoder) of layers or units applies convolution to increase abstractness or compression. The most abstract feature values are then output to another segment (i.e., decoder). The other segment of layers or units then applies transposed-convolution to decrease abstractness or compression. The encoder (convolutional) and decoder (transposed-convolutional) network forms a "U" shape with one vertical being encoding, another vertical being decoding, and the connection between being passing features at a greatest level of compression or abstractness from the encoder to the decoder. Any now known or later developed U-net architectures may be used. Skip connections, such as passing features at other scales than the greatest compression, may be provided. Other fully convolutional networks may be used.

At act A220, the latent space 431 is input into the decoder network 402 of the neural network 400. The decoder network 402 is configured to generate a first segmented image.

At act A230, a first value is calculated based on a comparison of the segmented image and a ground truth segmented image. The results relative to the ground truth and the error for reconstruction for the network are back-projected to learn the features that work best. In one embodiment, a L2-norm loss is used to optimize the network. Other error functions may be used. In one embodiment, the weights of the network are randomly initialized, but another initialization may be used. End-to-end training, such as of the encoder and decoder without a discriminator, is performed, but one or more features may be set. Batch normalization, dropout, and data augmentation are not used, but may be. The optimization is with the RMSprop optimizer, but other optimization functions (e.g., Adam, SGD, etc.) may be used. During the optimization, the different distinguishing features are learned.

At act A240, the latent space 431 (feature data) is input into a discriminator network 411. The discriminator network 411 is configured to classify the feature data as acquired from a first domain or second domain. In an embodiment, a convolutional network structure is used for the discriminator network 411. The discriminator network 411 receives feature data generated by the encoder network 401. The feature data is propagated through a plurality of convolutional layers with for example, the image dimension down and the channel dimension multiplied. Each convolutional layer 435 is followed by rectifiers. The final layer 435 returns a classification label of (0) for feature data from a first domain or (1) for feature data from a second domain. Instead of a binary classification label, the final layer 435 may return a classification score. For example, the score may include a range of 0 to 1 with scores closer to 0 indicating feature data from the first domain and scores closer to 1 indicating feature data from the second domain.

At act A250, a second value is calculated based on a second loss function for the classification. The second loss function may be calculated based on a Wasserstein or Cramer distance. The Wasserstein value is a measure of the distance between two probability distributions over a region. The Wasserstein value may also be referred to as the earth mover's distance. The two probability distributions may be interpreted as two different ways of piling up a certain amount of dirt over the region D. The earth mover's distance is the minimum cost of turning one pile into the other; where the cost is assumed to be amount of dirt moved times the distance by which it is moved.

The competition or adversarial relationship between the encoder network 401 and the discriminator network 411 may be defined by:

$$\min_G \max_D \mathbb{E}_{x \sim P_r}[\log(D(x))] + \mathbb{E}_{\tilde{x} \sim P_g}[\log(1 - D(\tilde{x}))], \quad \text{Equation 1}$$

where Pr is the data distribution and Pg is the model distribution implicitly defined by x=G(z), z~p(z) where the input z to the generator network 401 is sampled from some simple noise distribution p, such as the uniform distribution or a spherical Gaussian distribution.

The Wasserstein distance W(q, p), is defined as the minimum cost of transporting mass in order to transform the distribution q into the distribution p (where the cost is mass times transport distance). W(q, p) is continuous everywhere and differentiable almost everywhere. The discriminator value function is constructed using a Kantorovich-Rubinstein duality to obtain:

$$\min_G \max_{D \in \mathcal{D}} \mathbb{E}_{x \sim P_r}[D(x)] + \mathbb{E}_{\tilde{x} \sim P_g}[D(\tilde{x})] \quad \text{Equation 2}$$

where the cost function for the discriminator network 411 is the set of 1-Lipschitz functions and Pg is the model distribution implicitly defined by x=G(z), z p(z). Under an optimal discriminator, minimizing the value function with respect to the generator network 401 parameters minimizes W (Pr, Pg). The value function results in a critic function that includes a gradient. The weights of the critic function may be clipped to lie within a compact space. The critic function is calculated using the Wasserstein value and provided to the encoder network 401.

At act A260, the encoder network 401 is adjusted as a function of the first value and the second value. The discriminator network 411 and the decoder networks 402 may also be adjusted. The encoder network 401 is adjusted based on the value provided by the loss function from the discriminator network 411. The discriminator network 411 may also be adjusted as a function of a comparison between input ground truth data and the predicted output. The two networks contest one another, the discriminator network 411 attempts to distinguish feature data between domains, and the generator network 401 attempts to generate image data that confuses the discriminator network 411 into classifying all the images as "ground truth". At the end of training process, the generator network 401 generates feature maps that are indistinguishable between domains.

The acts A210-260 may be repeated until the first and second loss function converge. At act A270, the machine outputs a trained network. The machine-learned network is a neural network incorporating the deep learned features for the various units and/or layers of the network and/or the relationships of input features to the output. The collection of individual features forms a feature or feature set for generating a segmented image from MR data. For a convolutional neural network, the features are provided as nodes of the feature units in different levels of abstraction or compression. The nodes define convolution kernels trained to extract the features. Once trained, a matrix, kernels, or other trained network is output. The machine learned network includes definitions of convolution kernels, links, weights, pooling, and/or other characteristics of the network trained to generate the image from input MR data with or without input metadata and/or auxiliary map. The machine learned detector is output to a network or memory. For example, the neural network as trained is stored in a memory for transfer and/or later application.

Once the network is trained, the trained network may be applied. The trained network with defined or learnt features is used to extract from previously unseen input MR data with or without other inputs (e.g., auxiliary map and/or metadata). The machine-learned network uses extracted features from the MR data with or without other information to generate a segmented image that is protocol independent.

Figure 8:
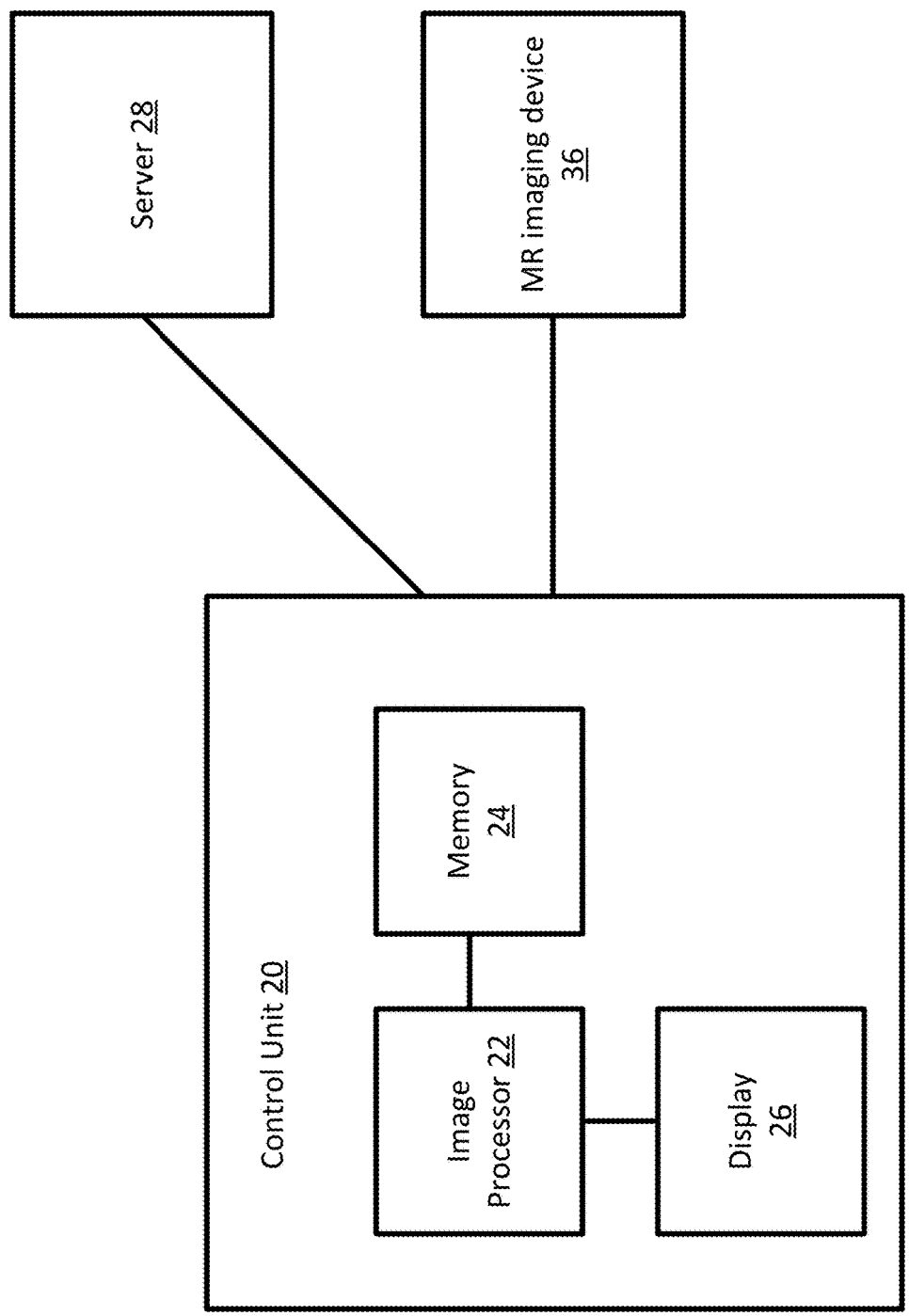
FIG. 8 depicts one embodiment of a control unit for generating protocol invariant segmented images from MR data.

FIG. 8 depicts one embodiment of a control unit for generating protocol invariant segmented images from MR data. The control unit includes an image processor 22, a memory 24, and a display 26. The control unit 20 may be connected with a server 28 and an MR imaging device 36. Additional, different, or fewer components may be provided. For example, network connections or interfaces may be provided, such as for networking between the control unit 20 and server 28. A workstation with a user interface may be provided for an operator to input data.

The MR imaging device 36 may be similar to the MR imaging device as depicted in FIG. 1. The MR imaging device 36 is configured to acquire MR data that may be processed into one or more images by the control unit 20. The control unit 20 may provide commands to the MR imaging device 36. Alternatively, the MR imaging device 36 may function entirely on its own without any input from the control unit 20.

The image processor 22 (or processor) is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for processing an image. The processor 22 is a single device or multiple devices operating in serial, parallel, or separately. The processor 22 may be a main processor of a computer, such as a laptop or desktop computer, or may be a processor for handling some tasks in a larger system, such as in the MRI system. The processor 22 is configured by instructions, design, hardware, and/or software to perform the acts discussed herein.

The server 28 may be co-located with the control unit 20 or may be located remotely. The server 28 may connect to the MRI system 100 or control unit 20 via a network. The network is a local area, wide area, enterprise, another network, or combinations thereof. In one embodiment, the network is, at least in part, the Internet. Using TCP/IP communications, the network provides for communication between the processor 24 and the server 28. Any format for communications may be used. In other embodiments, dedicated or direct communication is used.

The server 28 may include the processor 24 or group of processors. More than one server 28 or control unit 20 may be provided. The server 28 is configured by hardware and/or software. In one embodiment, the server 28 performs machine learning of the encoder, decoder, and discriminator networks. The server 28 may acquire and the memory 24 may store MR data from multiple different MRI systems.

The processor 24 and/or server 28 are configured to perform the acts discussed above for generating protocol independent images. The processor 24 and/or server 28 may access and implement the code stored in memory 24.

The memory 24 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 24 is part of the control unit 20, part of a database, part of another system, a picture archival memory, or a standalone device. The memory 24 may store image data from the MRI system. The memory 24 may store an instruction set or computer code configured to implement an encoder network 401, a decoder network, and when training, a discriminator network 411.

The memory 24 includes an instruction set or computer code for implementing the machine learnt networks. In an embodiment, the memory 24 only includes a trained encoder network 401 and decoder network 401. Alternatively, for training, the discriminator network 411 may also be stored in memory 24.

In an embodiment, a deep learning generator is stored in the memory 24 that includes both the trained encoder network 401 and decoder network 401. The deep learning generator includes an initialization layer 435 (or layers) that defines a number of feature maps to start with from the input images directly. The initialization layer 435 may also be a full generative network that is trained with the main brain extraction task, in which case the initialization layer 435 may serve as normalization.

The deep learning generator extracts features from input images and reconstructing the segmentation of the brain and its tissue. The deep learning generator first includes an encoder that generates a latent space 431, or a compact representation of the input images. The encoder is followed by a decoder that uses the latent space 431 to get to the specific task of reconstructing the brain and tissue masks. The encoder and decoder are symmetrical, using the same number of pooling (downsampling/upsampling) steps and therefore allowing connections between encoding and decoding stages. Between each pooling step, blocks are defined as succession of layers which also use skip connections. The number of layers in each block may be defined and a growth rate is set to increase the number of feature maps for each consecutive layer 435 in a block. A final layer 435 in the network includes a smoothing layer 435 with a kernel size of one that cleans up the images. To train the deep learning generator, categorical cross-entropy drives the loss to either separate the brain, or the tissues or everything at once.

In an embodiment, an adversarial network is uses for domain adaptation. Using the latent space 431 features, a discriminator network 411 is applied to determine out whether the features comes from one domain (one protocol) or another. The optimization drives the discriminator to maximize its loss, and such that it becomes unable to recognize which protocol or domain the data comes from. Training may be done sequentially, with one batch of data with segmentation ground truth with data from original domain and the other one with domain ground truth. The initial domain may be the domain that includes data with the most details, as that domain may be easier to adapt to less detailed acquisition.

In an embodiment, the memory 24 further stores a network for feature refinement that uses adversarial training with a Wasserstein or Cramer distance on the decoder output. The training may be done end to end while the encoder is being trained or after the encoder is trained using the domain adaptation, thus focusing on refining the weights of the decoder. A conditional discriminator network may be used that determines whether the segmentation that is presented as input is generated or ground truth. In addition, the original input is presented as a condition to do such a classification. The goal is that the discriminator cannot differentiate between real and fake segmentation. In another embodiment, the original image is synthesized from the produced segmentation. An additional generative network is used to synthesize the original with a set of loss to minimize the errors between the original input and the synthesized input from generated segmentation.

The memory 24 or other memory is alternatively or additionally a non-transitory computer readable storage medium storing data representing instructions executable by the programmed processor 22 for generating protocol independent segmented image data 439. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

The display 26 may be configured to display images to an operator. The display 26 may augment the images with additional information or overlays. The display 26 may be configured to display the images in two dimensions, three dimensions, or, for example, in augmented or virtual reality scenarios.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A method for generating domain independent magnetic resonance images in a magnetic resonance imaging system, the method comprising:
    scanning a patient by the magnetic resonance imaging system to acquire magnetic resonance data;
    inputting the magnetic resonance data to a machine learnt generator network trained to extract features from input magnetic resonance data and reconstruct domain independent images using the extracted features;
    generating, by the machine learnt generator network, a domain independent magnetic resonance image from the input magnetic resonance data; and
    displaying the domain independent magnetic resonance image,
    wherein the machine learnt generator network comprises an encoder configured to generate a compact representation of the input magnetic resonance data and a decoder configured to reconstruct the domain independent image from the compact representation,
    wherein the machine learnt generator network is trained using a loss function that is calculated as a combination of a first value, computed from a first loss function provided by the decoder and a second value, computed from a second loss function provided by a first adversarial learnt network trained to classify concatenated features from the compact representation as either from a first domain or a second domain.

2. The method of claim 1, wherein the second loss function is calculated as a function of a Wasserstein distance.

3. The method of claim 1, wherein the second loss function is calculated as a function of a Cramer distance.

4. The method of claim 1, wherein the first domain represents ground truth data.

5. The method of claim 1, wherein the machine learnt generator network is further trained using a second adversarial learnt network trained to classify generated domain independent images as generated by the machine learnt generator network or ground truth images.

6. The method of claim 1, wherein the domain independent magnetic resonance image is a segmented image.

7. The method of claim 6, wherein the segmented image comprises a segmented brain image including boundaries for at least white matter, grey matter, and cerebrospinal fluid.

* * * * *